(12) United States Patent
Ohzawa

(10) Patent No.: US 9,919,104 B2
(45) Date of Patent: Mar. 20, 2018

(54) BIOLOGICAL INFORMATION MEASUREMENT DEVICE

(71) Applicant: PANASONIC HEALTHCARE HOLDINGS CO., LTD., Minato-Ku, Tokyo (JP)

(72) Inventor: Akiyoshi Ohzawa, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 357 days.

(21) Appl. No.: 14/372,022

(22) PCT Filed: Feb. 15, 2013

(86) PCT No.: PCT/JP2013/000827
§ 371 (c)(1),
(2) Date: Jul. 14, 2014

(87) PCT Pub. No.: WO2013/121791
PCT Pub. Date: Aug. 22, 2013

(65) Prior Publication Data
US 2014/0358082 A1 Dec. 4, 2014

(30) Foreign Application Priority Data

Feb. 17, 2012 (JP) .................................. 2012-032325

(51) Int. Cl.
*A61M 5/172* (2006.01)
*A61M 5/168* (2006.01)
*G06F 19/00* (2018.01)
*A61B 5/00* (2006.01)
*A61M 5/142* (2006.01)

(52) U.S. Cl.
CPC ........... *A61M 5/172* (2013.01); *A61B 5/4839* (2013.01); *A61M 5/142* (2013.01);
(Continued)

(58) Field of Classification Search
CPC .. A61M 5/172; A61M 5/142; A61M 5/16831; A61M 5/16877; A61M 5/1723;
(Continued)

(56) References Cited

U.S. PATENT DOCUMENTS 8,127,046 B2 2/2012 Grant et al.
2008/0177900 A1 7/2008 Grant et al.
(Continued)

FOREIGN PATENT DOCUMENTS

JP 2008-546496 A 12/2008
JP 2009-529930 A 8/2009
(Continued)

OTHER PUBLICATIONS

An office action from the corresponding Japanese Patent Application No. 2014-500115 dated Aug. 4, 2015.
(Continued)

*Primary Examiner* — Bhisma Mehta
*Assistant Examiner* — Hamza Darb
(74) *Attorney, Agent, or Firm* — Shinjyu Global IP

(57) ABSTRACT

The protrusion relates to a device comprising a main body case having a sensor mounting component, a measurement component that is connected to the sensor mounting component, a controller that is connected to this measurement component, and a display component that is connected to this controller. A communication component that is connected to the controller communicates pharmaceutical injection information and non-pharmaceutical-injection information to a specific pump. The controller performs communication at a first output when communicating non-pharmaceutical-injection information to the pump, and performs communication at a second output that is smaller than the first output when communicating pharmaceutical injection information to the pump.

8 Claims, 5 Drawing Sheets

(52) U.S. Cl.
CPC .... *A61M 5/16831* (2013.01); *A61M 5/16877* (2013.01); *A61M 5/1723* (2013.01); *G06F 19/3468* (2013.01); *A61M 2202/07* (2013.01); *A61M 2205/3569* (2013.01); *A61M 2205/3576* (2013.01); *A61M 2205/502* (2013.01); *A61M 2205/60* (2013.01)

(58) Field of Classification Search
CPC ...... A61M 2202/07; A61M 2205/3576; A61M 2205/502; A61M 2205/60; A61M 2205/3569; A61B 5/4839; G06F 19/3468
See application file for complete search history.

(56) References Cited

U.S. PATENT DOCUMENTS

| | | |
|---|---|---|
| 2009/0018495 A1 | 1/2009 | Panduro |
| 2009/0062778 A1* | 3/2009 | Bengtsson ............ A61B 5/4839 604/890.1 |
| 2009/0138207 A1* | 5/2009 | Cosentino .......... A61B 5/14532 702/19 |
| 2011/0319813 A1* | 12/2011 | Kamen ............. A61M 5/14244 604/66 |
| 2012/0277668 A1* | 11/2012 | Chawla ................... A61M 5/00 604/66 |
| 2012/0302849 A1 | 11/2012 | Grant et al. |

FOREIGN PATENT DOCUMENTS

| | | |
|---|---|---|
| JP | 2010-511430 A | 4/2010 |
| JP | 2011-508637 A | 3/2011 |
| WO | 2009/088956 A2 | 7/2009 |

OTHER PUBLICATIONS

The International Search Report of Int'l Appln. No. PCT/JP2013/000827 dated May 14, 2013.

* cited by examiner

BIOLOGICAL INFORMATION MEASUREMENT DEVICE

PRIORITY

This application claims priority to International Application PCT/JP2013/000827, with an international filing date of Feb. 15, 2013 which claims priority to Japanese Patent Application No. JP2012-032325 filed on Feb. 17, 2012. The entire disclosures of International Application PCT/JP2013/000827 and Japanese Patent Application No. JP2012-032325 are hereby incorporated herein by reference.

TECHNICAL FIELD

The present invention relates to a biological information measurement device that provides a pharmaceutical dose amount to a pharmaceutical injection device, and is used, for example, when insulin is injected to a diabetic patient.

BACKGROUND

A conventional biological information measurement device of this type was configured as follows. Specifically, this device comprised a main body case having a sensor mounting component, a measurement component that was connected to the sensor mounting component, a controller that was connected to this measurement component, a display component that was connected to this controller, and a communication component that was connected to the controller and communicated pharmaceutical injection information and non-pharmaceutical-injection information to a pharmaceutical injection device (such as an insulin pump) (see Patent Literature 1: JP2010-511430A, for example).

A biological information measurement device is configured to perform one-on-one communication between just a pharmaceutical injection device (such as an insulin pump) paired with this biological information measurement device. For example, the biological information measurement device of user A is only able to communicate with the pharmaceutical injection device (such as an insulin pump) that user A himself is wearing.

More specifically, when the biological information measurement device is one that measures blood glucose levels, for example, the insulin dose based on the blood glucose level measured by this biological information measurement device is communicated to the paired insulin pump.

Since the biological information measurement device can communicate only with a paired pharmaceutical injection device (such as an insulin pump), the insulin pump will not operate with a blood glucose level measured by anyone else, which gives the user greater peace of mind. That is, the insulin pump of user A will not operate with information from the biological information measurement device of user B.

However, if user A should accidentally use the biological information measurement device of user B, then the insulin pump of user B will end up operating even though the blood glucose level of user A was measured.

For instance, if users A and B are in the same family, they will usually use biological information measurement devices of the same manufacturer and model, and as a result, it is conceivable that user A will accidentally use the biological information measurement device of user B as in the above scenario.

If this should happen, the insulin pump of user B will operate improperly on the basis of the blood glucose level of user A.

SUMMARY

The present invention comprises a measurement component that is connected to a sensor mounting component, a controller that is connected to this measurement component, a display component that is connected to this controller, and a communication component that is connected to the controller and communicates pharmaceutical injection information and non-pharmaceutical-injection information to a pharmaceutical injection device.

If the controller determines to communicate non-pharmaceutical-injection information to the pharmaceutical injection device, communication is performed with the transmission output set to a first output, and if pharmaceutical injection information is to be communicated to the pharmaceutical injection device, communication is performed with the transmission output set to a second output.

Specifically, with the present invention, when a user A uses the biological information measurement device of a user B, for example, the insulin dose (pharmaceutical injection information) based on the blood glucose level of user A will be communicated to the insulin pump of user B. However, this communication is performed at a second output that has a smaller transmission output. That is, the communication of pharmaceutical injection information is switched to near field communication.

Accordingly, even though the biological information measurement device of user B communicates, this communication will not reach the insulin pump of user B, and therefore the insulin pump of user B will not accidentally operate on the basis of the blood glucose level of user A. That is, when user A measures his blood glucose level, for the above-mentioned near field communication to succeed, user A must move the biological information measurement device of user B close to the insulin pump of user A. This is a state in which the biological information measurement device of user B being accidentally used by user A is far away from the insulin pump of user B. That is, it is a state in which the wireless communication distance is limited, preventing communication with another pharmaceutical injection device (the insulin pump of user B). Accordingly, the insulin pump of user B will not operate, and as a result, improper operation of the pharmaceutical injection device can be prevented.

After this, user A will notice that he is accidentally using the biological information measurement device of user B from an error message displayed on the biological information measurement device of user B that user A is currently holding, and will then switch over to his own biological information measurement device. At this point user A will bring his own biological information measurement device close to his own insulin pump, and thereby conclude communication. As a result, the insulin pump of user A can be operated on the basis of the blood glucose level of user A.

DETAILED DESCRIPTION

The biological information measurement device in a first embodiment of the present invention will now be described through reference to the drawings. It will be apparent to those skilled in the art from this disclosure that the following descriptions of the embodiments are provided for illustration only and not for the purpose of limiting the invention as defined by the appended claims and their equivalents.

First Embodiment

Figure 1:
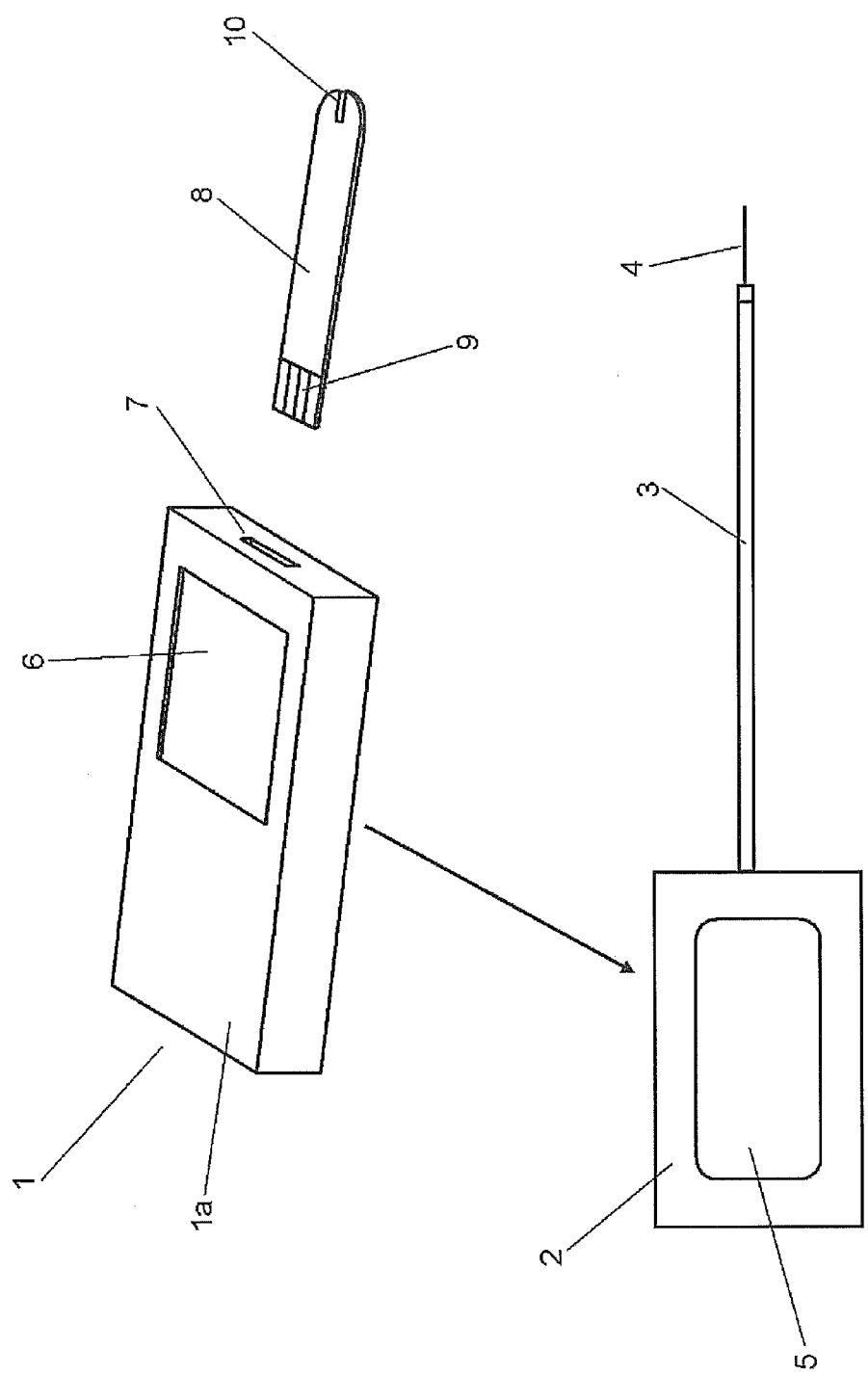
FIG. 1 is a diagram of the usage state of a biological information measurement device in a first embodiment of the present invention.

As shown in FIG. 1, a measurement device 1, which is an example of a biological information measurement device that measures a glucose level from blood, communicates an insulin dose (an example of pharmaceutical injection information) based on the measured blood glucose level to an insulin pump (an example of a pharmaceutical injection device; hereinafter referred to as "pump") 2.

A pharmaceutical syringe (not shown) containing insulin is removably mounted to a pharmaceutical syringe mounting component (not shown) in the interior of the pump 2. The pharmaceutical contained in this pharmaceutical syringe is administered to the patient through a needle 4 and a tube 3 connected to the pharmaceutical syringe mounting component, on the basis of the insulin dose communicated from the measurement device 1.

The needle 4 is inserted into the abdomen or the subcutaneous fat of the abdomen of the user, and the pump 2 can automatically administer insulin on the basis of the pharmaceutical injection information from the measurement device 1. The pump 2 is generally attached around the waist and under the clothing of the user. A display component 5 is provided to the front of the pump 2.

The measurement device 1 will be described.

A display component 6 is provided to the top face of a main body case 1a of the measurement device 1, and a sensor mounting component 7 is provided to the distal end side of the main body case 1a. A connection terminal 9 of a flat and rectangular blood glucose level sensor 8 is mounted to this sensor mounting component 7. In this state, when blood is deposited on a deposition component 10 provided to the end of the blood glucose level sensor 8 on the opposite side from the connection terminal 9, the blood glucose level at that point is measured and displayed on the display component 6.

Figure 2:
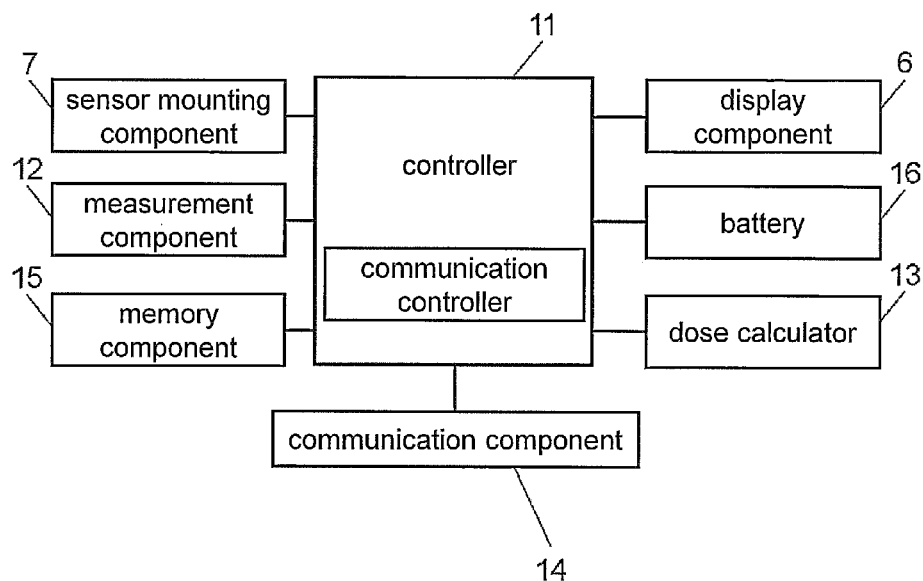
FIG. 2 is a control block diagram of the biological information measurement device in the first embodiment.

FIG. 2 is a control block diagram of the measurement device 1.

The display component 6 and the sensor mounting component 7 of the measurement device 1 are connected to a controller 11. This controller 11 is connected to a measurement component 12 that measures the blood glucose level of the blood glucose level sensor 8 shown in FIG. 1 and mounted to the sensor mounting component 7, and a dose calculator 13 that calculates the dose of insulin corresponding to the blood glucose level measured by the measurement component 12. The measurement component 12 is also connected to the sensor mounting component 7.

The controller 11 is also connected to a communication component 14 that communicates the insulin dose calculated by the dose calculator 13 to the pump 2 in FIG. 1. Communication between the measurement device 1 and the pump 2 is performed wirelessly. This controller 11 is also connected to a memory component 15 and a battery 16.

Figure 3:
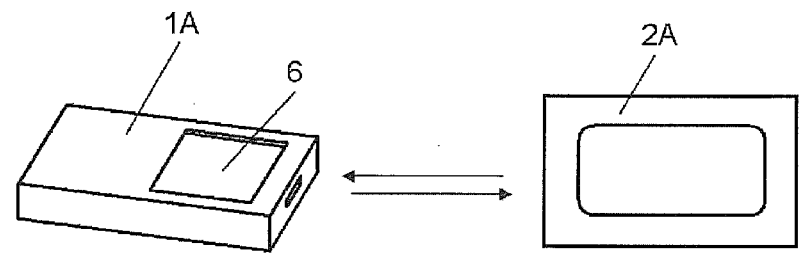
FIG. 3 is a diagram of the usage state of the biological information measurement device in the first embodiment.
Figure 3:
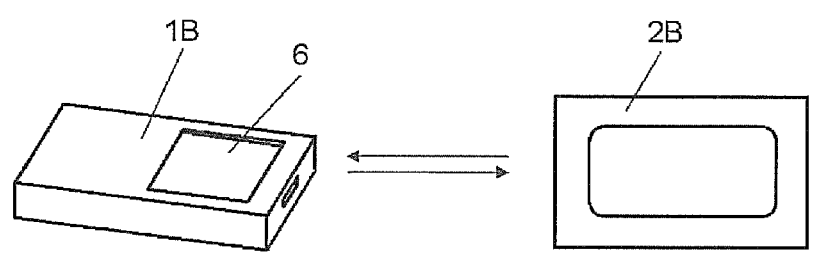

FIG. 3 is a diagram illustrating communication between the measurement device 1 and the pump 2.

As shown in FIG. 3, for example, the measurement device 1A of user A is paired with a pump 2A, and the measurement device 1A communicates only with the pump 2A. Similarly, the measurement device 1B of user B is paired with a pump 2B, and the measurement device 1B communicates only with the pump 2B.

That is, the pump 2B of user B will not operate with information from the measurement device 1A of user A.

The measurement device 1A and the pump 2A, and the measurement device 1B and the pump 2B are paired together, and this pairing is accomplished, for example, by exchanging individual identification information with each other (such as a 10-digit number; hereinafter referred to as an ID). The ID of the pump 2A here is stored in the memory component 15 of the measurement device 1A, and the ID of the pump 2B is stored in the memory component 15 of the measurement device 1B.

The IDs of the pump 2A and the pump 2B are affixed as stickers, for example, on the surface of each. Similarly, the IDs of the measurement device 1A and the measurement device 1B are affixed as stickers on the surface of each.

This pairing of the measurement device 1A with the pump 2A, and of the measurement device 1B with the pump 2B is always carried out one time prior to performing wireless communication. After this pairing, communication will only be performed between the members of each pair. This communication method is a standard technique that comes under the Bluetooth standard, and therefore will not be described in detail here.

The operation with the above configuration will now be described.

First, in this embodiment, there are two kinds of data communicated from the measurement device 1 to the pump 2: important data (pharmaceutical injection information) and ordinary data (non-pharmaceutical-injection information).

Important data (pharmaceutical injection information) is information related to pharmaceutical injection by the pump 2, examples of which include insulin dose information (an example of pharmaceutical dose information), blood glucose level information for calculating the insulin dose (an example of pharmaceutical dose calculation information), and the name and address of the owner of the pump 2 (an example of individual information).

Ordinary data (non-pharmaceutical-injection information), on the other hand, is information other than important data (pharmaceutical injection information), an example of which is setting information about the device. More specifically, this is setting information such as the time setting of the pump 2, changes to the display, and the display of a log.

When this ordinary data is wirelessly sent from the measurement device 1 to the pump 2, just as in the past, the controller 11 of the measurement device 1 performs communication with the transmission output of the communication component 14 set to a first output that covers a wide range (such as 1 meter). This makes the device more convenient for the user.

The communication of important data (pharmaceutical injection information), which is a characteristic feature of this embodiment, will now be described in detail through reference to the flowchart in FIG. 4.

We will describe here an example in which the measurement device 1 is used to measure a blood glucose level, and this is communicated to the pump 2.

Figure 5:
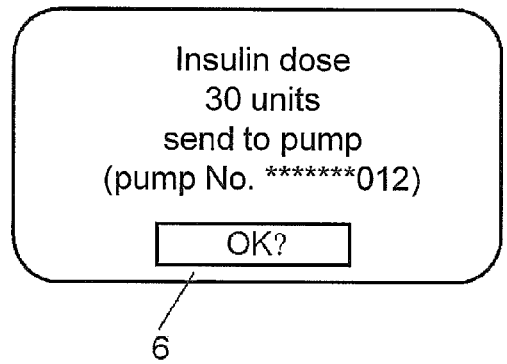
FIG. 5 is a diagram showing the display on the display component of the biological information measurement device in the first embodiment.

First, as discussed above, the patient's blood glucose level is measured with the measurement component 12 of the measurement device 1 (step S1), and the insulin dose corresponding to this blood glucose level is calculated by the dose calculator 13. Then, as shown in FIG. 5, the controller 11 displays "insulin dose 30 units: send to pump" as communication information on the display component 6. The units here refer to the insulin dose.

In this embodiment, prior to performing communication, the controller 11 acquires the 10-digit ID of the pump 2 stored in the memory component 15, and displays the last three digits (for example) on the display component 6 as "pump No. *****012." This allows the user to compare the ID displayed on the display component 6 with the ID written on the sticker of his own pump 2** and thereby confirm that they are a pair.

At this point, the controller 11 outputs the transmission output of the communication component 14 of the measurement device 1 as a first output that covers a wide range (such as 1 meter) (step S2).

After this, when the user presses the send button (not shown), the controller 11 determines whether or not the transmitted data is important data. Since the insulin dose being transmitted this time is insulin dose information, it is determined to be important data (step S3).

Then, the controller 11 determines whether or not the blood glucose level sensor 8 is still mounted to the sensor mounting component 7 (step S4). If the blood glucose level sensor 8 is still mounted, a message of "Remove sensor" is displayed on the display component 6 to prompt the user to remove the blood glucose level sensor 8 from the sensor mounting component 7, and the system then waits for the blood glucose level sensor 8 to be removed (step S5).

This prevents the user from getting his clothes dirty. Specifically, as will be described below, the system switches to near field communication when important data is being communicated, so the user ends up moving the measurement device 1 closer to the pump 2. If the blood glucose level sensor 8 has been mounted to the sensor mounting component 7 at this point, the user's clothing may be soiled by the blood deposited on the deposition component 10 of the blood glucose level sensor 8. In view of this, in this embodiment the user is prompted to remove the blood glucose level sensor 8.

After it is confirmed that the blood glucose level sensor 8 has been removed from the sensor mounting component 7, the controller 11 switches the transmission output of the communication component 14 to the second output, which is smaller than the first output used for communicating ordinary data, in order to communicate the insulin dose (pharmaceutical injection information) to the pump 2. That is, the system switches to near field communication (step S6).

Figure 6:
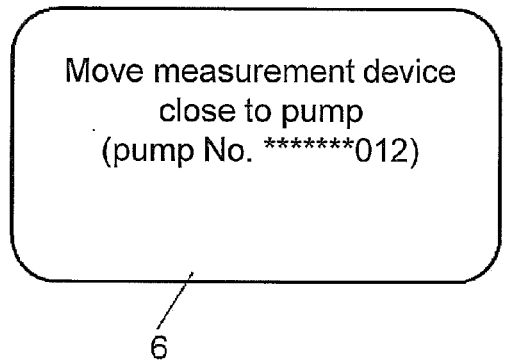
FIG. 6 is a diagram showing the display on the display component of the biological information measurement device in the first embodiment.

As shown in FIG. 6, the controller 11 then displays a message of "Move measurement device closer to pump" on the display component 6 to prompt the user to move the measurement device 1 near the pump 2. Here again, the last three digits of the ID of the pump 2 are displayed on the display component 6 as "pump No. *****012." This allows the user to compare the ID displayed on the display component 6 with the ID written on the sticker of his own pump 2 and thereby confirm that they are a pair (step S7**)

The communication component 14 detects that the pump 2 is its pair when the user moves the measurement device 1 close to the pump 2. More specifically, the paired pump 2 is requested to communicate, and communication becomes possible when there is a specific reaction from the paired pump 2. This detection takes 10 seconds, for example. The user holds the measurement device 1 close to the pump 2 for 10 seconds (step S8).

Figure 7:
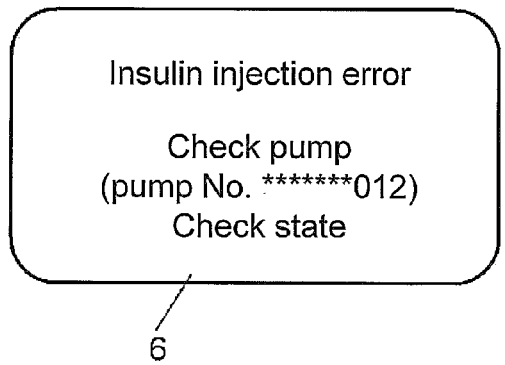
FIG. 7 is a diagram showing the display on the display component of the biological information measurement device in the first embodiment.

If the pump 2 cannot be detected, as shown in FIG. 7, the controller 11 displays messages of "Check pump" and "pump No. *****012" along with the error message "insulin injection error" on the display component 6. The last three digits of the ID of the pump 2 are displayed on the display component 6**, for example.

At this point, if the user should unintentionally use the measurement device 1 of another person and bring it close to his own pump 2, naturally that pump 2 cannot be detected.

That is, the other person's measurement device 1 being unintentionally used by the user is brought close to the user's own pump 2, and is far away from the other person's pump 2. Accordingly, the other person's pump 2 will not work, and the pump 2 that belongs to the other person's pharmaceutical injection device will not improperly operate on the basis of the user's own blood glucose level.

As a result, improper operation of the pump 2 (pharmaceutical injection device) can be prevented.

Furthermore, when the user is unintentionally using the measurement device 1 of another person, the display component 6 displays the ID of the other person's pump 2 as "pump No. *******222."

The user can check that the pairing is correct by comparing the ID displayed on the display component 6 with the ID written on the sticker of his own pump 2. This check allows the user to notice that he is using the wrong measurement device 1 and to halt its use.

After the processing in step S9, the controller 11 returns to step S8 and again detects the pump. These steps S8, S9, and S10 show the retry procedure, and this retry is carried out a plurality of times (such as twice). If the user is using his own measurement device 1, the system can return to the normal communication procedure (step S12; discussed below) by bringing the measurement device 1 close to the pump 2 during this retry.

However, upon the third retry, the controller 11 determines that there is a communication error and displays the communication error information of FIG. 7 again on the display component 6 (step S11). After this, the transmission output of the communication component 14 is returned to its original level, that is, it is switched to the first output used for the communication of ordinary data (step S14), and the communication is ended (step S15).

When the user is using his own measurement device 1 and brings this measurement device 1 close to the pump 2, in step S8 the user's own pump 2 is detected, the insulin dose is sent from the communication component 14 of the measurement device 1 to the pump 2 (step S12), and the controller 11 displays a message of "transmission complete" on the display component 6 (step S13).

After this, the controller 11 returns to the original transmission output of the communication component 14, that is, switches to the first output used for the communication of ordinary data (step S14), and ends communication (step S15).

Next, the communication of ordinary data will be described.

When ordinary data (non-pharmaceutical-injection information, that is, information other than pharmaceutical injection information) is communicated (step S16), if the user checks the communication information and presses the send button (not shown) (step S2), the controller 11 determines that the data is ordinary data (step S3) and detects the paired pump 2.

For this detection, the communication component 14 of the measurement device 1 communicates at a first output that covers a wide range (such as 1 meter), so the paired pump 2 can be detected right away (step S8).

After this, the device setting information is sent from the communication component 14 of the measurement device 1 to the pump 2 (step S12) at the first output that covers a wide range (such as 1 meter), and the controller 11 displays a message of "transmission complete" on the display component 6 (step S13).

After this, the controller 11 ends communication (step S15) in the state of the first output (step S14).

As described above, the characteristic feature of this embodiment is that when important data (one or more of pharmaceutical dose information, pharmaceutical dose calculation information, and individual information) is sent to the pump 2, the transmission output of the communication is switched to the second output, which is smaller than the first output used for the communication of ordinary data. That is, the communication is switched to near field communication.

As a result, improper operation of the pump 2 can be prevented.

Specifically, in the state in FIG. 3, if users A and B are in the same family, they will usually use measurement devices 1 of the same manufacturer and model, and as a result, it is conceivable that user A will accidentally use the measurement device 1B of user B as discussed above.

If this should happen, an insulin dose (pharmaceutical injection information) based on the blood glucose level of user A will be sent to the pump 2B of user B. However, this communication is performed at the second output to which the transmission output of the communication is reduced. That is, the communication is switched to near field communication.

Therefore, even though there is communication of the measurement device 1B of user B, this communication will not reach the pump 2B of user B, and therefore the pump 2B of user B will not accidentally operate on the basis of the blood glucose level of user A. That is, when user A measures his blood glucose level, for the above-mentioned near field communication to succeed, user A must move the measurement device 1B of user B close to the pump 2A of user A. This is a state in which the measurement device 1B of user B being used by user A is far away from the pump 2B of user B. That is, it is a state in which the wireless communication distance is limited, preventing communication with the pump 2B (another pharmaceutical injection device). Accordingly, the pump 2B of user B will not operate, and as a result, improper operation of the pump 2B (pharmaceutical injection device) can be prevented.

Figure 4:
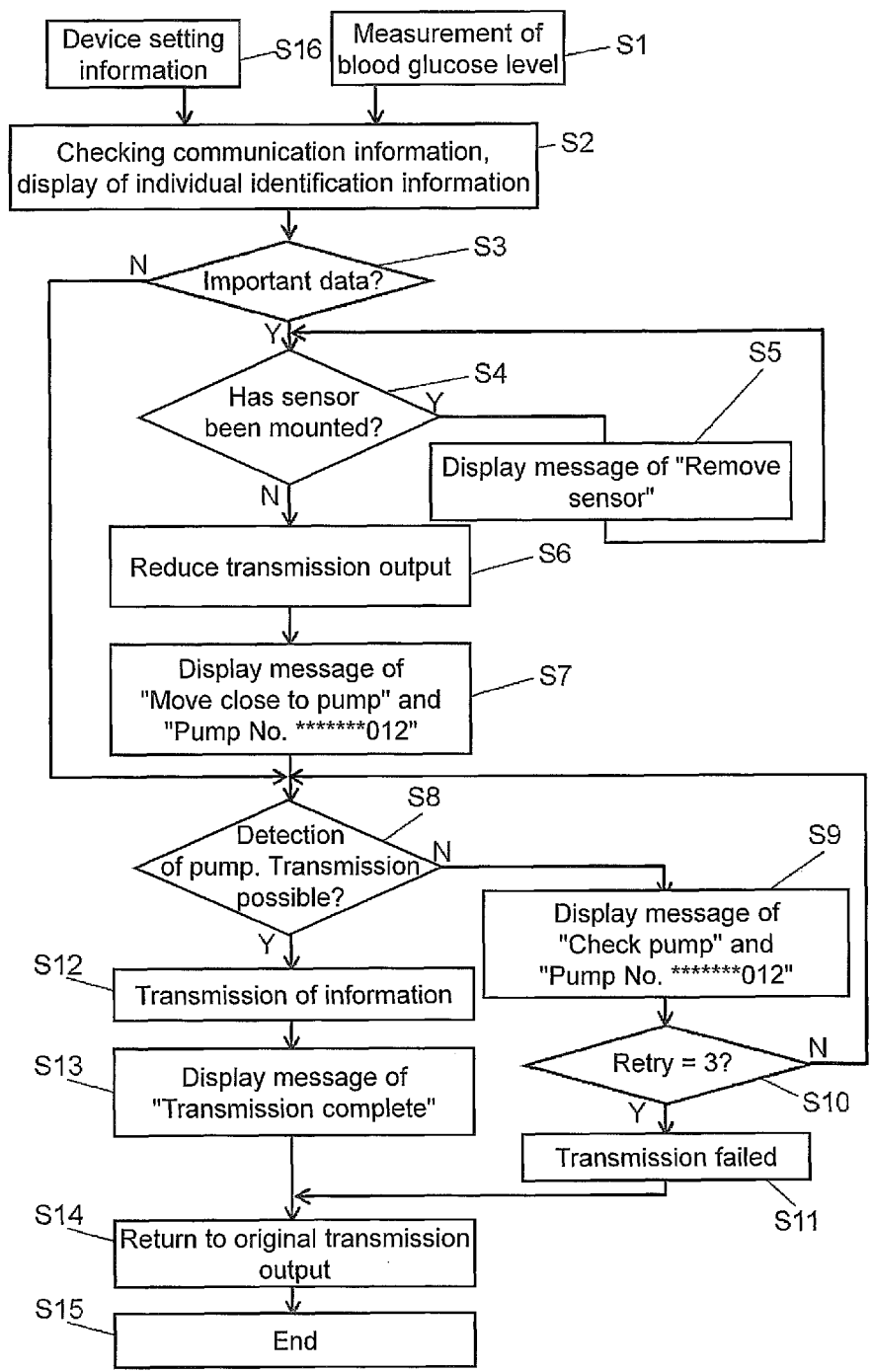
FIG. 4 is an operational flowchart of the biological information measurement device in the first embodiment.

In this embodiment, in steps S2, S7, and S9 in FIG. 4, the ID of the pump 2 are displayed as "pump No. *******222" on the display component 6 when the measurement device 1 of another person is accidentally used.

Therefore, in FIG. 3, for example, when user A is unintentionally using the measurement device 1B of user B, the ID of the pump 2B of user B is displayed on the display component 6.

Here, if user A compares the displayed ID with the ID of his own pump 2A, naturally the two IDs will be different. In view of this, user A will notice that he is not using his own measurement device 1A, and can stop using the wrong one. Thus, if user A can notice the incorrect usage from the display on the display component 6, he will be able to halt any further such use.

Therefore, user A will no longer operate the pump 2B of user B, and as a result the improper operation of the pump 2B (pharmaceutical injection device) can be prevented.

Figure 8:
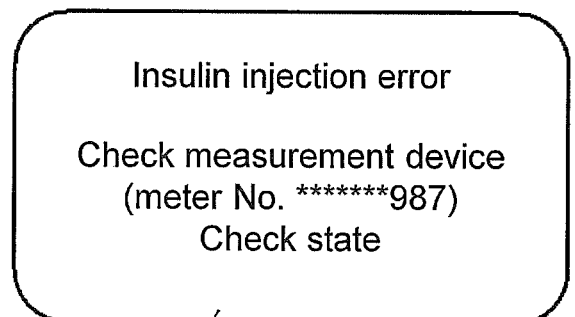
FIG. 8 is a diagram showing the display on the display component of the biological information measurement device in the first embodiment.

In this embodiment, the ID of the pump 2 was displayed on the display component 6, but instead of the ID of the pump 2, the ID of the measurement device 1 may be displayed as "meter No. *******987," for example, as shown in FIG. 8. Since the ID of the measurement device 1 is affixed by a sticker to the front of the measurement device 1, it is easy to check.

Figure 9:
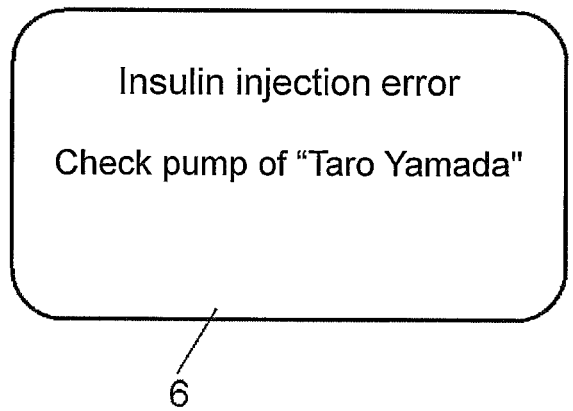
FIG. 9 is a diagram showing the display on the display component of the biological information measurement device in the first embodiment.

As shown in FIG. 9, information associated with the ID of the pump 2 or the ID of the measurement device 1 (such as the name or nickname of the user) may be displayed. In this case, using the name or nickname of the user makes it easier for the user to spot incorrect usage.

The pump 2 is placed under the clothing, as mentioned above. Therefore, displaying the name or nickname of the user on the measurement device 1, which the user has close at hand, allows the user to notice incorrect usage without having to check the pump 2 worn under his clothing.

As a result, improper operation of the pump 2 (pharmaceutical injection device) can be prevented.

INDUSTRIAL APPLICABILITY

As discussed above, the present invention is expected to find wide application as a biological information measurement device used when insulin is administered to a diabetic patient, for example.

The invention claimed is:

1. A biological information measurement device comprising:
a main body case including a sensor mounting component, a measurement component, a controller, a display component, and a communication component;
the measurement component connected to the sensor mounting component;
the controller connected to the measurement component;
the display component connected to the controller; and
the communication component connected to the controller and, wherein the communication component:
transmits information to a pharmaceutical injection device, the information including pharmaceutical injection information and non-pharmaceutical-injection information,
performs a first transmission output of the communication component when transmitting the non-pharmaceutical-injection information to the pharmaceutical injection device, and
performs a second transmission output of the communication component when transmitting the pharmaceutical injection information to the pharmaceutical injection device only when the communication component and the pharmaceutical injection device are in near field communication, wherein:
the controller further determines whether a communication from the communication component to the pharmaceutical injection device at the second transmission output is possible, and
when the controller determines that the communication from the communication component to the pharmaceutical injection device at the second transmission output is impossible due to an improper matching of the biological information measurement device and the pharmaceutical injection device, the display component either displays:
(1) individual identification information about the biological information measurement device belonging to a different user, or
(2) individual identification information about the pharmaceutical injection device along with the biological information measurement device belonging to the different user.

2. The biological information measurement device according to claim 1, wherein:
the pharmaceutical injection information is at least one of pharmaceutical dose information, pharmaceutical dose calculation information, and individual information.

3. The biological information measurement device according to claim 1, wherein:
when the controller is determining whether the communication from the communication component to the pharmaceutical injection device at the second transmission output is possible, the display component displays a message prompting removal of a sensor from the sensor mounting component.

4. The biological information measurement device according to claim 1, further comprising:
the controller is further configured to detect whether a sensor is mounted to the sensor mounting component.

5. A biological information measurement method comprising:
transmitting information to a pharmaceutical injection device from a communication component, the information including pharmaceutical information and non-pharmaceutical-injection information;
transmitting a first transmission output of non-pharmaceutical-injection information;
transmitting a second transmission output of pharmaceutical injection information only when the communication component and the pharmaceutical injection device are in near field communication; and
determining whether a communication to the pharmaceutical injection device at the second transmission output is possible, and
if the communication to the pharmaceutical injection device at the second transmission output is impossible due to improper matching of the biological information measurement device and the pharmaceutical injection device, displaying individual identification information about either:
(1) the biological information measurement device belonging to a different user, or
(2) individual identification information about the pharmaceutical injection device along with the biological information measurement device belonging to the different user on a display.

6. The biological information measurement method of claim 5, wherein:
the pharmaceutical injection information is at least one of pharmaceutical dose information, pharmaceutical dose calculation information, and individual information.

7. The biological information measurement method of claim 5, further comprising:
detecting whether a sensor is mounted to a sensor mounting component.

8. The biological information measurement method of claim 5, further comprising:
a biological information measurement device accepting a biological sample from a user;
a display of the biological information measurement device displaying a message prompting removal of a sensor if the sensor is mounted; and
a controller determining whether the second transmission output from the communication component to the pharmaceutical injection device is possible.

* * * * *